United States Patent [19] [11] 4,115,549
Scott [45] * Sep. 19, 1978

[54] COATING THE HAIR WITH A HEAT-SETTABLE COMPOSITION

[75] Inventor: Howard L. Scott, Philadelphia, Pa.

[73] Assignee: Widner College, Chester, Pa.

[*] Notice: The portion of the term of this patent subsequent to Apr. 13, 1993, has been disclaimed.

[21] Appl. No.: 676,616

[22] Filed: Apr. 13, 1976

Related U.S. Application Data

[63] Continuation-in-part of Ser. No. 86,597, Nov. 3, 1970, Pat. No. 3,949,764, which is a continuation-in-part of Ser. No. 721,158, Apr. 15, 1968, Pat. No. 3,568,685, which is a continuation-in-part of Ser. No. 386,730, Jul. 31, 1964, abandoned.

[51] Int. Cl.$^2$ ............................................. A61K 7/11
[52] U.S. Cl. ................................ 424/71; 8/127.51; 132/7; 424/DIG. 2; 424/70; 424/74; 424/78
[58] Field of Search ................................ 260/29, 6 F; 424/DIG. 2, 70, 71, 78, 74; 132/7; 8/127.51

[56] References Cited

U.S. PATENT DOCUMENTS

| | | | |
|---|---|---|---|
| 2,570,478 | 10/1951 | Pitzl | 260/78.5 |
| 2,613,193 | 10/1952 | Osdal | 260/29.6 F |
| 2,750,947 | 6/1956 | Gant | 424/71 X |
| 2,754,820 | 7/1956 | Brown et al. | 260/29.6 F |
| 2,782,790 | 2/1957 | Hersh et al. | 424/71 X |
| 2,787,274 | 4/1957 | Gant et al. | 424/71 X |
| 3,026,250 | 3/1962 | Coyner | 424/71 X |
| 3,157,562 | 11/1964 | Kine et al. | 260/29.4 X |
| 3,301,807 | 1/1967 | Hoashi | 260/29.6 F |
| 3,949,764 | 4/1976 | Scott | 132/7 |
| 3,972,998 | 8/1976 | Keiner | 424/70 |

*Primary Examiner*—Albert T. Meyers
*Assistant Examiner*—Vera C. Clarke
*Attorney, Agent, or Firm*—Arthur A. Jacobs

[57] ABSTRACT

A method of setting or coating hair, fur, synthetic or human in a predetermined condition, either straightened or curled, or waterproofed, which comprises coating the hair with a heat-settable coating composition containing a hardening and adhesive agent in oil and aqueous media, either with or without the addition of separate water-proofing agents, softening agents, and the like and then applying heat to the coated hair to set the coated hair in the selected condition.

4 Claims, No Drawings

COATING THE HAIR WITH A HEAT-SETTABLE COMPOSITION

This is a continuation-in-part of co-pending application Ser. No. 86,597, filed Nov. 3, 1970 now issued as U.S. Pat. No. 3,949,764, which is a continuation-in-part of Ser. No. 721,158, filed Apr. 15, 1968, now issued as U.S. Pat. No. 3,568,685, the latter being a continuation-in-part of application Ser. No. 386,730, filed July 31, 1964, and now abandoned.

This invention relates to the treatment of fibers such as synthetic or natural hair, or synthetic fur, and it particularly relates to the treatment of synthetic fibers to give the appearance of human hair, as well as to give synthetic fur the appearance of real animal fur, and as well as to the curling of straight hair or the straightening of extremely tightly curled hair, either human or synthetic.

Natural or synthetic hair or fur fibers can be treated with a composition containing essentially a specific type of water-repellent agent and a specific type of substantive hardening and adhesive agent, or a combination of mixed hardening and adhesive agents. In addition, there may also be included a slipping agent and an emollient. Such treatment results in a very satisfactory setting of the hair or fur, either in a straightened or curled form, and gives the hair a substantive and durable resistance to the effects of moisture.

A most satisfactory treatment may be obtained by utilizing the hardening agent, by itself, as the essential treating agent, and that this will provide an effective degree of durable coating and waterproofing without the use of other water-repellent agents. It is preferred that the hardening agent be used together with various types of softening agents which are also water-repellent. In addition, slipping agents and emollients may also be used when desired or needed.

The hardening agents utilized in the present invention include the following:

(1) p,p'-methylenedianiline; (2) a copolymer obtained by polymerizing a mixture of (a) about 0.5-25% by weight of itaconic acid, (b) 3-4% by weight of at least one polymerizable compound selected from the group consisting of acrylonitrile, alkyl esters of acrylic and methacrylic acids having from 1 to 18 carbon atoms in the alkyl group, phenyl methacrylate, methacrylonitrile, methyl vinyl ketone and vinyl chloride, and (c) 35-96.5% by weight of vinylidene chloride, the proportions being selected to total 100%; (3) water-insoluble copolymers obtained by the emulsion copolymerization of about 0.5-6% by weight of either N-methylolacrylamide, N-methylolmethacrylamide, or mixtures thereof with about 0.5-25% by weight of either acrylamide or methacrylamide, and having a molecular weight of 100,000 to 10,000,000; (4) copolymers of acrylonitrile and styrene as produced; and (5) a solution of water-soluble, oxidizing resin containing about 50% by weight solids, having a viscosity of SX (Gardner Holdt at 25° C.) and a pH of between 6.9 and 7.3 at 25° C; as well as (6) chlorophyll a having the structure $C_{55}H_{72}MgN_4O_5$ and chlorophyll b which have the structure $C_{55}H_{70}MgN_4O_6$.

Another effective hardening and adhesive agent, which may also serve as a flame retardant, is one or more of the following: (1) a vinyl chloride-vinylidene chloride copolymer; (2) vinyl chloride polymers plasticized with alkyl aryl phosphate plasticizers at levels of 25 and 35 parts per hundred polymer respectively; (3) a vinyl chloride polymer plasticized with 35 parts dioctyl phthalate per 100 parts polymer; (4) unplasticized vinyl chloride copolymers; (5) unplasticized vinyl chloride homopolymer; (6) vinyl chloride-acrylic latexes; and (7) a vinyl chloride/butadiene-acrylonitrile polyblend latex.

The hardening agent is utilized in the proportions from 1-85% by volume of the total composition, said composition including water and/or oil as at least one of the other other ingredients. The hair should then have a durable effective hardening and adhesive agent to affect a durable coating to keep the hair curled or straight.

It is preferable to apply the composition to the fibers or hair by spraying, dipping, rubbing, or the like, and then to immediately dry the treated hair at a temperature of between 110°-160° F.

As indicated above, the hardening and adhesive agent may be used by itself in various type media in the above mentioned proportions. The composition is prepared by simple admixture, preferably under agitation, at room temperature and pressure.

Although, as stated above, the hardening and adhesive agent may be used by itself to obtain a satisfactory coating composition, it has been found that the addition of a very small amount of a softening agent materially enhances the appearance and quality of the finished product. This softening agent is generally utilized in a proportion of about 0.2-5% by volume of the total composition.

Among the softening agents preferably used is an aqueous dispersion of N-methylol stearamide, wherein the compound is present in the dispersion in a concentration of about 20-40% by weight, preferably about 20-35% by weight.

Another softening agent, which has a water-repellent function as well, is a complex of aluminum and myristic acid and which has the following structure:

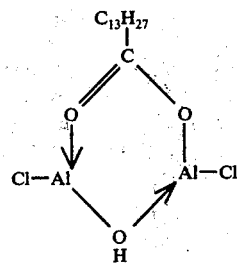

In this complex, the aluminum groups anchor to the treated surfaces while the myristic group orients outward.

Yet another softening agent is a Werner type chromium complex having the structure:

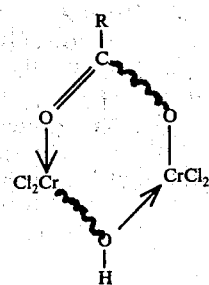

Where R is either $C_{17}H_{35}$ or $C_{13}H_{27}$.

Another softening agent is a Werner chromium complex, usually in isopropanol solution, that differs from the above complexes through partial polymerization. The chromium atoms polymerize through "olation" bridges to form

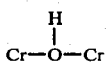

groups. On drying, hydrolysis and condensation occur to the point where the polymer is condensed through —O— bridges with the surface as follows:

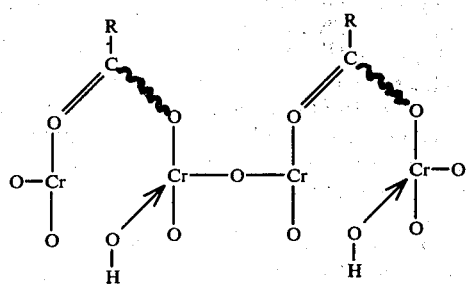

If a separate water-repellent agent is used, it is preferably one which is preferably used in a proportion of about 2–55% by volume, and consists of (a) a wax-polymer emulsion wherein the ratio of wax to polymer is about 3:1, the polymer being a copolymer which consists of (1) about 20–80% by weight of an amino group containing comonomer having the structure:

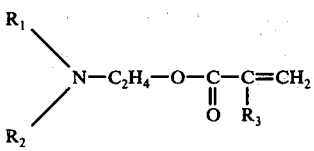

Where $R_1$ and $R_2$ are selected from the group consisting of lower alkyl and cycloalkyl that include $R_1$ and $R_2$, and $R_3$ is selected from the group consisting of H and $CH_3$, and (2) 10–80% by weight of a comonomer having the structure:

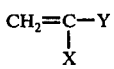

where X is a member of the group selected from H and $CH_3$ and Y is a member selected from the polar group consisting of nitrile, aliphatic acyloxy having from 1–18 carbon atoms and alkoxycarbonyl having from 1–18 carbon atoms, said copolymer having an intrinsic viscosity in benzene at 30° C. of from 0.04–0.5.

The slipping agent, utilized in a proportion of about 0.1–10% by volume may be any one of a number of fluoro resins. The product, as used herein, is a polytetrafluoroethylene having a molecular weight of between about 1,000,000 to 10,000,000, and a viscosity greater than $10^{10}$ poises at 380° C. Also utilizable is a vinylidene fluoride resin having a molecular weight of between about 300,000 and 600,000 and having the structure:

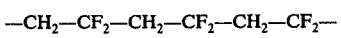

The emollient, which may be used in a proportion of from 0 to 60.00% by volume, may be lanolin or any equivalent substance.

All of the compositions embodying the present invention may be prepared by mixing together the desired proportions of all the components at room temperature and pressure.

In the operation of one of the present processes, the hair strands are coated with the composition, either by spraying, dipping, rubbing, etc., and the coated hair is wrapped around the device acting like a comb to disentangle the hair and separate the strands into a multiplicity of hanks or groups, whereby the individual strands in each hank are more easily accessible to the heated cylindrical surface.

A sufficient amount of heat is supplied to cure the composition, effecting a crystallization thereof. This forms a relatively permanent set or coating. The heat required for this purpose is between about 110°–160° F. depending on the type of hair or fiber being processed and on the type of composition used.

The process is repeated with each portion of the hair until the entire head of hair, wig, fur, or the like has been treated.

The following examples illustrate the invention, without, however, limiting it except as claimed:

EXAMPLE NO. 1

75% by volume of p,p'-methylenedianiline was mixed, at room temperature and pressure, with 8% by volume of lanolin and with 17% water, the mixture taking place under agitation until a homogeneous cream-like substance was produced.

EXAMPLE NO. 2

47.5 parts by weight of ethyl acrylate, 3 parts by weight of a non-ionic dispersing agent (a 70% aqueous solution of a tertoctylphenoxypolyethoxyethanol containing an average of about 35 oxyethylene units in the molecule) and 100 parts by weight of water were cooled to 15° C. and then agitated. Then 0.085 parts by weight of ammonium persulfate and 0.08 parts by weight of sodium hydrosulfite were added. As soon as the temperature began to rise, 2.5 parts by weight of itaconic acid, dissolved in 44 parts by weight of water, was added over a period of 8 minutes. As polymerization proceeded, the temperature rose in 17 minutes to a maximum of 56° C. The dispersion was stirred until it reached room temperature.

59% by volume of the above dispersion was mixed, under agitation, at room temperature and pressure, with 2.3% by volume of the Werner type complex, 4% by volume of the wax-polymer emulsion described above, 1% by volume of polytetrafluoroethylene, and 16.7 by volume water. Agitation was continued until a heavy grease-like cream was obtained.

EXAMPLE NO. 3

To a solution of 300 parts of 2-diethylaminoethyl methacrylate and 700 parts of octadecyl methacrylate in 1000 parts of molten paraffin wax, maintained at 75° C., in a suitable vessel equipped with an agitator, are added 10 parts of 2,2¹-azodiisobutyronitrile in small increments over a period of 6 to 10 hours. After the last addition of the polymerization initiator, the reaction mass is held at 75° C. for two hours, and the temperature is then raised to 100° C. and held at that temperature for about one-half hour. The charge is then diluted with 2,000 parts by weight of molten paraffin wax, to give a wax:copolymer ratio of 3:1. All parts herein are by weight.

Into 100 parts by weight of the above wax-copolymer composition, melted by heating to between 65° and 70° C., 4 parts by weight of glacial acetic acid are stirred. The wax-copolymer mass is then slowly added to 294 parts by weight of water kept under vigorous agitation with a high shear mixer, and maintained at 65° to 70° C. Agitation is then continued for a sufficient time to complete the emulsification. The resulting product is then cooled to room temperature. The product has a molecular weight of between about 20,000 and 80,000 and a viscosity of about 16 centipoises at 80° F. (Brookfield).

In one operation, the composition of Example 3 was applied to a human head of hair until the hair was completely coated. Thereafter, each increment of the hair was heated to 140° F for about 1 second at which time crystallizatin of the composition occurred. After the entire head of hair had been processed, the treated hair was styled in a desirable manner.

The composition of Example 3 was applied to strands of modacrylic fibers. After crystallization of the composition occurred, the fibers had the texture of first class fur.

It is also understood that wig fibers of human hair like texture can also be made as above.

The invention claimed is:

1. A method of treating natural or synthetic hair or fur which comprises coating said hair or fur with an effective amount sufficient to set said hair or fur of a composition comprising a hardening and adhesive agent in either an aqueous or oil media, said hardening and adhesive agent being in a concentration of about 1–85% by volume and being selected form the group consisting of (1) p,p′-methylenedianiline; (2) a copolymer of (a) about 0.5–25% by weight of itaconic acid, (b) 3–4% by weight of at least one polymerizable compound selected from the group consisting of acrylonitrile, alkyl esters of acrylic and methacrylic acids having from 1 to 18 carbon atoms in the alkyl group, phenyl methacrylate, methacrylonitrile, methyl vinyl ketone and vinyl chloride, and (c) 35–96.5% by weight of vinylidene chloride, the proportions being selected to total 100% (3) water insoluble copolymers obtained by the emulsion copolymerization of about 0.5–6 parts by weight of either N-methylolacrylamide, N-methylolmethacrylamide, or mixtures thereof, with about 0.5–25 parts by weight of either acrylamide or methacrylamide, and having a molecular weight of 100,000 to 10,000,000; (4) a copolymer of acrylonitrile and styrene wherein a 50% by weight solution has a viscosity of SX (Gardner Holdt) at 25° C; (5) chlorophyll a having the formula $C_{55}H_{72}MgN_4O_5$ and chlorophyll b which has the formula $C_{55}H_{70}MgN_4O_6$; (6) a vinyl chloride-vinylidene chloride co-polymer; (7) vinyl chloride polymers plasticized with alkyl aryl phosphate plasticizers at levels of 25 and 35 parts per 100 parts of polymer respectively; (8) a vinyl chloride polymer plasticized with 35 parts dioctyl phthalate per 100 parts of polymer; (9) vinyl chloride-acrylic latexes; and (10) vinyl-chloride/butadiene-acrylonitrile polyblend latex.

2. A natural or synthetic hair or fur treating composition comprising a hardening and adhesive agent in either an aqueous or oil media, said hardening and adhesive agent being in a concentration of about 1–85% by volume and being selected from the group consisting of (1) p,p′-methylenedianiline; (2) a copolymer of (a) about 0.5–25% by weight of itaconic acid, (b) 3–4% by weight of at least one polymerizable compound selected from the group consisting of acrylonitrile, alkyl esters of acrylic and methacrylic acids having from 1 to 18 carbon atoms in the alkyl group, phenyl methacrylate, methacrylonitrile, methyl vinyl ketone and vinyl chloride, and (c) 35–96.5% by weight of vinylidene chloride, the proportions being selected to total 100%; (3) water insoluble copolymers obtained by the emulsion copolymerization of about 0.5–6 parts by weight of either N-methylolacrylamide, N-methylolmethacrylamide, or mixtures thereof, with about 0.5–25 parts by weight of either acrylamide or methacrylamide, and having a molecular weight of 100,000 to 10,000,000; (4) a copolymer of acrylonitrile and styrene wherein a 50% by weight solution has a viscosity of SX (Gardner Holdt) at 24° C; (5) chlorophyll a having the formula $C_{55}H_{72}MgN_4O_5$ and chlorophyll b which has the formula $C_{55}H_{70}MgN_4O_6$ (6) a vinyl chloride-vinylidene chloride co-polymer; (7) vinyl chloride polymers plasticized with alkyl aryl phosphate plasticizers at levels of 25 and 35 parts per 100 parts of polymer respectively; (8) a vinyl chloride polymer plasticized with 35 parts dioctyl phthalate per 100 parts of polymer; (9) vinyl chloride-acrylic latexes; and (10) vinyl-chloride/butadiene-acrylonitrile polyblend latex; and a softening agent, said softening agent being present in a proportion of about 0.1 to 5% by volume and being selected from the group consisting of (a) a compound having the formula:

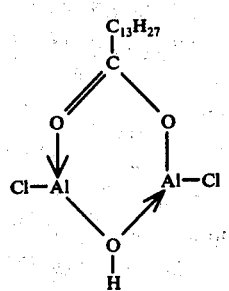

(b) a comound having the formula:

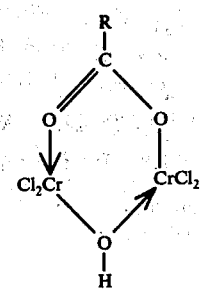

and (c) a compound having the formula:

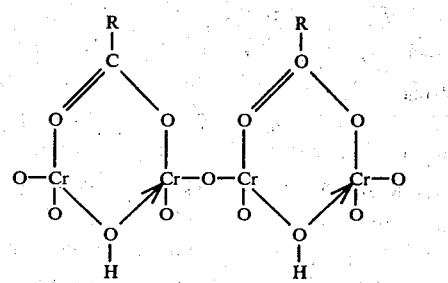

wherein R is $C_{13}H_{27}$ or $C_{17}H_{35}$.

3. A natural or synthetic hair or fur treating composition comprising a hardening and adhesive agent in either an aqueous or oil media, said hardening and adhesive agent being in a concentration of about 1–85% by volume and being selected from the group consisting of (1) p,p'-methylenedianiline; (2) a copolymer of (a) about 0.5–25% by weight of itaconic acid, (b) 3–4% by weight of at least one polymerizable compound selected from the group consisting of acrylonitrile, alkyl esters of acrylic and methacrylic acids having from 1 to 18 carbon atoms in the alkyl group, phenyl methacrylate, methacrylonitrile, methyl vinyl ketone and vinyl chloride, and (c) 35–96.5% by weight of vinylidene chloride, the proportions being selected to total 100%; (3) water insoluble copolymers obtained by the emulsion copolymerization of about 0.5–6 parts by weight of either N-methylolacrylamide, N-methylolmethacrylamide, or mixtures thereof, with about 0.5–25 parts by weight of either acrylamide or methacrylamide, and having a molecular weight of 100,000 to 10,000,000; (4) a copolymer of acrylonitrile and styrene wherein a 50% by weight solution has a viscosity of SX (Gardner Holdt) at 25° C; (5) chlorophyll a having the formula $C_{55}H_{72}MgN_4O_5$; and chlorophyll b which has the formula $C_{55}H_{70}MgN_4O_6$; (6) a vinyl chloride-vinylidene chloride co-polymer; (7) vinyl chloride polymers plasticized with alkyl aryl phosphate plasticizers at levels of 25 and 35 parts per 100 parts of polymer respectively; (8) a vinyl chloride polymer plasticized with 35 parts dioctyl phthalate per 100 parts of polymer; (9) vinyl chloride-acrylic latexes; and (10) vinyl chloride/butadiene-acrylonitrile polyblend latex; and about 1–50% by volume of a wax polymer emulsion wherein the ratio of wax to polymer is about 3:1, the polymer being a copolymer which consists of (1) about 15–19% by weight of an amino group containing comonomer having the structure:

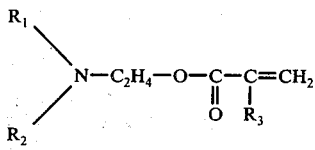

where $R_1$ and $R_2$ are selected from the group consisting of lower alkyl and cycloalkyl that include $R_1$ and $R_2$; $R_3$ is selected from the group consisting of H and $CH_3$; and (2) 10–85% by weight of a comonomer having the structure:

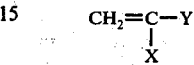

where X is a member selected from the group consisting of H and $CH_3$ and Y is a member selected from the group consisting of nitrile, aliphatic acyloxy having from 1–18 carbon atoms and alkoxycarbonyl having from 1–18 atoms; said last copolymer having intrinsic viscosity in benzene at 39° C. of from 0.04–0.5.

4. A natural or synthetic hair or fur treating composition comprising a hardening and adhesive agent in either an aqueous or oil media, said hardening and adhesive agent being in a concentration of about 1–85% by volume and being selected from the group consisting of (1) p,p'-methylenedianiline; (2) a copolymer of (a) about 0.5–25% by weight of itaconic acid, (b) 3–4% by weight of at least one polymerizable compound selected from the group consisting of acrylonitrile, alkyl esters of acrylic and methacrylic acids having from 1 to 18 carbon atoms in the alkyl group, phenyl methacrylate, methacrylonitrile, methyl vinyl ketone and vinyl chloride, and (c) 35–96.5% by weight of vinylidene chloride, the proportions being selected to total 100% (3) water insoluble copolymers obtained by the emulsion copolymerization of about 0.5–6 parts by weight of either N-methylolacrylamide, N-methylolmethacrylamide, or mixtures thereof, with about 0.5–25 parts by weight of either acrylamide or methacrylamide, and having a molecular weight of 100,000 to 10,000,000; (4) a copolymer of acrylonitrile and styrene wherein a 50% by weight solution has a viscosity of SX (Gardner Holdt) at 25° C; (5) chlorophyll a having the formula $C_{55}H_{72}MgN_4O_5$ and chlorophyll b which has the formula $C_{55}H_{70}MgN_4O_6$; (6) a vinyl chloride-vinylidene chloride co-polymer; (7) vinyl chloride polymers plasticized with alkyl aryl phosphate plasticizers at levels of 25 and 35 parts per 100 parts of polymer respectively; (8) a vinyl chloride polymer plasticized with 35 parts dioctyl phthalate per 100 parts of polymer; (9) vinyl chloride-acrylic latexes; and (10) vinyl-chloride/butadiene-acrylonitrile polyblend latex; and about 0.01–10% by volume of a member selected from the group consisting of (a) polytetrafluoroethylene having a molecular weight of between about 1,000,000 to 10,000,000 and a viscosity greater than $10^{10}$ poises at 380° C., and (b) vinylidene fluoride resin having a molecular weight of between about 300,000 and 600,000 and having the structure:

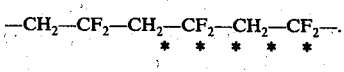

* * * * *